US006617432B1

(12) United States Patent
Getzenberg

(10) Patent No.: US 6,617,432 B1
(45) Date of Patent: Sep. 9, 2003

(54) NUCLEAR MATRIX PROTEINS POLYNUCLEOTIDE SEQUENCES ENCODING THEM AND THEIR USE

(75) Inventor: Robert H. Getzenberg, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/418,839

(22) Filed: Oct. 15, 1999

(51) Int. Cl.[7] .............................................. A61K 39/00
(52) U.S. Cl. ....................... 530/358; 530/300; 530/350; 530/387.1; 530/388.8; 435/7.1
(58) Field of Search ................................ 530/350, 300, 530/358, 387.1, 388.8; 435/7.1

(56) References Cited

U.S. PATENT DOCUMENTS 5,874,539 A * 2/1999 Coffey et al. ............. 530/387.1

FOREIGN PATENT DOCUMENTS

| WO | WO87/03910 | 7/1987 |
| WO | WO93/09437 | 5/1993 |
| WO | WO94/00573 | 1/1994 |
| WO | WO94/18222 | 8/1994 |
| WO | WO95/16919 | 6/1995 |
| WO | WO97/16206 | 9/1997 |

OTHER PUBLICATIONS

Getzeuberg, RH et al. Cancer Res 51: 6514–6520 (1991).*
Herbert et al. The Dictionary of Immunol., AP, 4th ed., p. 58, 1995.*
Greenspan, Nature Biotech. 7: 936–937, 1999.*
Miyanaga, N., et al., "Nuclear Matrix Proteins as a Urine for Transitional Cell Carcinoma of the Bladder". The Journal of Urology Supplement, vol. 153, No. 4 (XP-002068914).
Merrifield, S., et al., "The Performance of the NMP22™ Test Kit: A Quantitative Enzyme Immuno–Assay for Bladder Cancer", Tumor Biology, 17 (suppl 1) (1996). (XP-002068915).
Getzenberg, R., et al., "Bladder Cancer–associated Nuclear Matrix Proteins", Cancer Research vol. 56, No. 7, pp. 1690–1694, (1996), (XP002068894).
Konety, B.R., et al., "Identification of Nuclear Matrix Protein Alterations with Renal Cell Carcinoma", The Journal of Urology, vol. 159, No. 4, pp. 1359–1363 (1998). (XP002068895).
Eberharter A., et al., "Nuclear Matrix of the lower eukaryote Physarum polycephalum and the mammalian epithelial LLC–PK, cell line—A comprehensive investigation of different preparation procedures", vol. 212, No. 2 pp. 573–580 (1992). (XP02068893).

Keesee, S.K., et al., "Utilization of Nuclear Matrix Proteins for Cancer Diagnosis", Critical Reviews in Eukaryotic Gene Expression, vol. 6, NO. 2&3, pp. 189–214 (1996). (XP002069158).
Getzenberg, R. H., "Nuclear Matrix and the Regulation of Gene Expression: Tissue Specificity", Journal of Cellular Biochemistry, vol. 55, pp. 22–31 (1994).
Berezney, R., et al., "Identification of a Nuclear Protein Matrix", Biochemical and Biophysical Research Communications, vol. 60, No. 4 (1974).
Fey, E.G., et al., "The Nuclear Matrix: Defining Structural and Functional Roles", Eukaryotic Gene Expression, pp. 127–143 (1991).
Fey, E.G., et al., "Tumor promoters induce a specific morphological signature in the nuclear matrix–intermediate filament scaffold of Madin–Darby canine kidney (MDCK) cell colonies", Proc. Natl. Acad. Sci. USA, vol. 81, pp. 4409–4413 (1984).
Fey, E.G., et al., "Nuclear Matrix proteins reflect cell type of origin in cultured human cells", Proc. Natl. Acad. Sci. USA, vol. 85, pp. 121–125 (1988).
Fey, E.G., et al., "Epithelial Cytoskeletal Framework and Nuclear Matrix–Intermediate Filament Scaffold: Three–dimensional Organization and Protein Composition", The Journal of Cell Biology, vol. 98, pp. 1973–1984 (1984).
Weidner, N., et al., "Rapid Communication, Localization of Nuclear Matrix Proteins (NMPs) in Multiple Tissue Types with NM–200.4™ (An Antibody Strongly Reactive with NMPs Found in Breast Carcinoma)", American Journal of Pathology, vol. 138, No. 6, pp. 1293–1298 (1991).
Huse, W.D., et al., "Generation of a Large Combinatorial Library of the Immunoglobulin Repertoire in Phage Lambda", Research Article, pp. 1275–1281 (1989).
Mullinax, R.L., et al., "Identification of human antibody fragment specific for tetanus toxoid in a bacteriophage λ immunoexpression library", Proc. Natl. Acad. Sci. USA, vol. 87, pp. 8095–8099 (1990).
Diener, E., et al., "Specific Immunosuppression by Immunotoxins Containing Daunomycin", Science, vol. 231, pp. 148–150 (1986).

(List continued on next page.)

Primary Examiner—Susan Ungar
Assistant Examiner—Minh Tam Davis
(74) Attorney, Agent, or Firm—Foley & Lardner

(57) ABSTRACT

Nuclear matrix proteins (NMP) which are characterized by a defined expression in tissue, particularly prostate tissue, are provided. These NMPs are useful markers in diagnosing and monitoring the stage of malignancy of a cell and treating cell proliferative disorders associated with the NMP. Also provided are substantially purified polypeptides and nucleotide sequences encoding the NMPs of the invention.

2 Claims, No Drawings

OTHER PUBLICATIONS

Greiner, J.W., "Recombinant Interferon Enhances Monoclonal Antibody—Targeting of Carcinoma Lesions in Vivo", *Reports*, pp. 895–898 (1987).

Wolff, B., et al., "The Use of Monoclonal Anti–Thy$_1$IgG$_1$ for Targeting of Liposomes to AKR–A Cells In Vitro and In Vivo", *Biochimical et Biophysica Acta*, vol. 802, pp. 259–273 (1984).

Weintraub, H.M., "Antisense RNA and DNA", *Scientific American*, pp. 40–46 (1990).

Cech, T.R., PhD., "Ribozymes and Their Medical Implications", *JAMA*, vol. 260, No. 20, pp. 3030–3034 (1988).

Haseloff, J., et al., "Simple RNA enzymes with new and highly specific endoribonuclease activities", *Nature*, vol. 334, pp. 585–591 (1988).

Bejany, D.E., et al. Malignant Vesical Tumors Following Spinal Cord Injury, *The Journal of Urology*, vol. 138, pp. 1390–1392 (1987).

Kaufman, J.M., et al., "Bladder Cancer and Squamos Metaplasia in Spinal Cord Injury Patients", pp. 967–971 (1977).

Melzak J., M.D., "The Incidence of Bladder Cancer in Paraplegia", *Paraplegia*, pp. 85–96.

Nyquist, R.H., M.D., et al., "Morality and Survival in Traumatic Myelof During Nineteen Years, from 1946 to 1965", *Paraplegia*, pp. 22–48.

El–Masri, W.S., "Bladder Cancer After Spinal Cord Injury", *International Medical Society of Paraplegia*, pp. 265–270 (1981).

Geisler, W.O., et al., "Survival In Traumatic Transverse Myelitis", *Paraplegia*, vol. 14, pp. 262–275 (1977).

Hackler, R.H., "A 25–Year Prospective Mortality Study In The Spinal Cord Injured Patient: Comparison With The Long–Term Living Paraplegic", *The Journal of Urology*, vol. 117, pp. 486–488 (1977).

Pound, C.R., et al., "Differential Nuclear Matrix Protein (NMP) Patterns In Normal Renal Tissue And Renal Cell Carcinoma (RCC)". 92$^{nd}$ Annual Meeting of the American Urological Association, New Orleans, LA, USA (1997) J. of Urol., vol. 157 (4 suppl.) (1997) (XP–002076374).

Konety, B.R., et al., "Characteristic Nuclear Matrix Protein Alterations In Renal Cell Carcinoma (RCC)". 92$^{nd}$ Annual Meeting of the American Urological Association, New Orleans, LA, USA (1997) J. of Urol., vol. 157 (4 suppl.) (1997) (XP–002076375).

Gordon, J.N., et al., "Altered Extracellular Matrices Influence Cellular Processes and Nuclear Matrix Organizations of Overlying Human Bladder Urothelial Cells", *Cancer Research*, vol. 53, pp. 4971–4977 (1993).

Cupo, J., "Electrophoretic analysis of nuclear matrix proteins and the potential clinical applications", *Elsevier Science Publisher B.V.*, pp. 389–406 (1991).

Partin, A.W., et al., "Nuclear Matrix Protein Patterns in Human Benign Prostatic Hyperplasia and Prostate Cancer", *Cancer Research*, vol. 53, pp. 744–746 (1993).

Russell, P.J. et al., "Preclinical studies of monoclonal antibodies for intravesical radioimmunotherapy of human bladder cancer," Cell biophysics, vols. 24/25, pp. 155–61 (1994).

Kingsley E.A. et al., "Characterisation of the anti–bladder––cancer monoclonal antibody BLCA–8: identification of its antigen as a neutral glycolipid," Cancer Immunology, Immunotherapy, vol. 41, No. 6, pp. 348–354 1995) (XP000872998).

Fradet Y., "Molecular and immunologic approaches in the management of bladder cancer," Urologic Clinics of North America, vol. 18, No. 3, pp. 515–524 (1991) (XP000881253).

Replogle–Schwab R. et al., "The utilization of nuclear proteins for cancer diagnosis," Critcial Reviews in Eukaryotic Gene Expression, vol. 6, Nos. 2–3, pp. 103–113 (1996) (XP000881255).

Pirtskalaishvili G. et al., "Use of urine–based markers for detection and monitoring of bladder cancer," Techniques in Urology, vol. 5, No. 4, pp. 179–184 (1999) (XP000881344).

J.E. Celis et al., "Expression of the transformation–sensitive protein "cyclin" in normal human epidermal basal cells and simian virus 40–transformed keratinocytes," Proc. Natl. Acad. Sci. USA, vol. 81, pp. 3128–3132 (1984).

J.E. Celis et al., "Intermediate filaments in monkey kidney TC7 cells: Focal centers and interrelationship with other cytoskeletal systems," Proc. Natl. Acad. Sci. USA, vol. 81, pp. 1117–1121 (1984).

R. G. DiScipio et al., "Nucleotide sequence of cDNA and derived amino acid sequence of human complement component C9," Proc. Natl. Acad. Sci. USA, vol. 81, pp. 7298–7302.

R.B. Merrifield, "Solid Phase Peptide Synthesis. I. The synthesis of a Tetrapeptide," J. Am. Chem. Soc., vol. 85, No. 14, pp. 2149–2154 (1963).

Stewart and Young, "Solid Phase Peptide Synthesis," Freeman Publ. 1969, pp. 27–61.

J.Y. Douillard et al., "Monoclonal Antibodies Specific Immunotherapy of Gastrointestinal Tumors," Hybridoma, vol. 5, Suppl. 1 (1986) pp. S139–S149.

Matritech NMP22® Test Kit (6/96) pp. 1–39.

R. Fraley et al. "New Generation liposomes: the engineering of an efficient vehicle for intracellular delivery of nucleic acids," Trends Biochem. Sci., vol. 6, pp. 77–80 (1981).

K. J. Pienta et al., "A Common Set of Nuclear Matrix Proteins in Prostate Cancer Cells", The Prostate, vol. 23, pp. 61–67, (1993).

B. R. Konety et al., "Characterization of a Metastatic Dunning Rat Prostate Tumor Specific Nuclear Matrix Protein (NMP) AM–1", Proceedings of the American Association For Cancer Research, vol. 37, p. 73, (1996) (Abstract).

* cited by examiner

SEQUENCE LISTING

```
<160> NUMBER OF SEQ ID NOS:  8

<210> SEQ ID NO 1
<211> LENGTH: 9
<212> TYPE: PRT
<213> ORGANISM: Rattus sp.

<400> SEQUENCE: 1

Ile Thr Gly Leu Asn Met Val Glu Met
  1               5

<210> SEQ ID NO 2
<211> LENGTH: 25
<212> TYPE: PRT
<213> ORGANISM: Rattus sp.

<400> SEQUENCE: 2

Tyr Gly Pro Gln Tyr Gly His Pro Pro Pro Pro Pro Pro Pro Pro Asp
  1               5                  10                  15

Tyr Gly Pro His Ala Asp Ser Pro Val
             20                  25

<210> SEQ ID NO 3
<211> LENGTH: 25
<212> TYPE: PRT
<213> ORGANISM: Rattus sp.

<400> SEQUENCE: 3

Ile Gln His Pro Ser Asn Val Leu His Phe Phe Asn Ala Pro Leu Glu
  1               5                  10                  15

Val Thr Glu Glu Asn Phe Phe Glu Ile
             20                  25

<210> SEQ ID NO 4
<211> LENGTH: 8
<212> TYPE: PRT
<213> ORGANISM: Rattus sp.

<400> SEQUENCE: 4

Asp Glu Ser Thr Leu Gln Gly Phe
  1               5
```

```
<210> SEQ ID NO 5
<211> LENGTH: 6
<212> TYPE: PRT
<213> ORGANISM: Rattus sp.

<400> SEQUENCE: 5

Ala Leu Gln Asp Lys Val
 1               5

<210> SEQ ID NO 6
<211> LENGTH: 14
<212> TYPE: PRT
<213> ORGANISM: Rattus sp.
<220> FEATURE:
<223> OTHER INFORMATION: Xaa = any, other or unknown amino acid

<400> SEQUENCE: 6

Arg Leu Xaa Xaa Xaa Thr Lys Pro Met Val Asn Leu Ile Lys
 1               5                  10

<210> SEQ ID NO 7
<211> LENGTH: 12
<212> TYPE: PRT
<213> ORGANISM: Rattus sp.

<400> SEQUENCE: 7

Val Ser Asn Thr Pro Leu Pro Gly Val Phe Thr Lys
 1               5                  10

<210> SEQ ID NO 8
<211> LENGTH: 12
<212> TYPE: PRT
<213> ORGANISM: Rattus sp.

<400> SEQUENCE: 8

Asn Leu Asp Leu Asp Ser Ile Ile Ala Glu Val Lys
 1               5                  10
```

NUCLEAR MATRIX PROTEINS POLYNUCLEOTIDE SEQUENCES ENCODING THEM AND THEIR USE

This invention was made with support from the University of Pittsburgh Cancer Institute and from NIH grant CA65463 to the University of Pittsburgh Cancer Institute.

BACKGROUND OF THE INVENTION

The present invention relates generally to nuclear matrix proteins, called "NMPs" here, and more specifically to novel nuclear matrix proteins of the prostate which are associated with cell-proliferative disorders.

The early diagnosis of prostate cancer is central to the effective treatment of the disease. In addition, the ability to differentiate disease with metastatic ability from prostate cancer that is not able to metastasize is important. Nuclear structural alterations are so prevalent in cancer cells that they are commonly used as a pathological marker of transformation for many types of cancer. Nuclear shape is determined in part by the nuclear matrix, the dynamic skeleton of the nucleus.

The nuclear matrix is the structural component of the nucleus that determines nuclear morphology, organizes the DNA in a three-dimensional fashion which is tissue specific, and has a central role in the regulation of a number of nuclear processes including the regulation of gene expression. The nuclear matrix has been demonstrated to play a central role in the regulation of important cellular processes such as DNA replication and transcription. Getzenberg, *J. Cell Biochem.* 55: 22–31 (1994). The nuclear matrix is the framework or scaffolding of the nucleus and consists of the peripheral laminas and pore complexes, an internal ribonucleic protein network, and residual nucleoli. Berezney et al., *Biochem. Biophys. Res. Comm.* 60: 141017 (1974). The nuclear matrix consists of approximately 10% of the nuclear proteins and is virtually devoid of lipids, DNA and histones. Fey et al., *Critical Reviews in Eukaryotic Gene Expression* 1: 127–44 (1991).

A majority of the known NMPs are common to all cell types and physiologic states. A number of laboratories have identified NMPs which may be unique to certain cell types or states. Mitogenic stimulation and the induction of differentiation have been demonstrated to alter the composition of nuclear matrix proteins and structure. The nuclear matrix contains a number of associated proteins that have been demonstrated to be involved in transformation. Berezney first showed that the nuclear matrix is altered in transformation, examining hepatoma nuclear matrix proteins. Berezney et al., *Cancer Res.* 39: 3031–39 (1979). Fey and Penman demonstrated that tumor promoters induce a specific morphologic signature in the nuclear matrix-intermediate filament scaffold of kidney cells. Fey et al., *Proc. Nat'l Acad. Sci.* USA 81: 859–66 (1984). Fey and Penman went on to demonstrate that the pattern of NMPs differed between normal and tumorigenic cell lines. Fey et al., loc. cit. 85: 121–25 (1989). An antibody to a nuclear matrix protein, termed NM-200.4, was raised from the breast carcinoma cell line T47D. Weidner et al.,*Am. J. Path.* 138: 1293–98 (1991). This antibody reacts strongly with human breast carcinoma specimens as well as specimens from lung, thyroid, and ovarian cancers, but does not react with normal epithelial cells of similar origin, raising the possibility of the use of certain anti-NMP antibodies as diagnostic tools.

U.S. Pat. No. 5,824,490 discloses certain nuclear matrix proteins associated with prostate tissue, including one denoted "PC-1" used to identify prostate cancer. When human prostate samples were examined, nuclear matrix proteins were identified that (1) were present only in the normal prostate and were missing in both prostate cancer and benign prostatic hyperplasia (BPR) (normal pattern), (2) were found only in the prostate cancer cells and missing in the normal prostate and BPH (prostate cancer pattern), and (3) were found in both normal and BPH samples but were absent from prostate cancers. See also Getzenberg et al., *Cancer Res.*, 1991(51):6514–20.

Additional nuclear matrix proteins associated with prostate tissue are disclosed in Partin et al., Cancer Res. 1993 (53): 744–746.

SUMMARY OF THE INVENTION

The present invention relates to novel nuclear matrix proteins that are able to differentiate cancerous cells from normal cells and metastatic cancer cells from non-metastatic disease, polynucleotide sequences encoding them, polynucleotide sequences hybridizing to the sequences encoding them, antibodies directed against them, and their methods of use. In particular, these proteins are useful for diagnosing and producing treatments for cell proliferative disorders of the prostate.

DETAILED DESCRIPTION OF THE PREFERRED EMBODIMENTS

According to one aspect, the present invention comprehends a purified nuclear matrix protein (NMP) or a fragment thereof, which is absent in normal prostate cells but present in cancerous prostate cells. Preferably, the protein of this embodiment is selected from the those, as described below, that are designated "D-1," "D-2," and "D-3." The proteins D-1, D-2, and D-3 are present in both metastatic and non-metastatic cancerous prostate cells.

According to another aspect, the present invention is directed to a purified NMP or a fragment thereof, which is present in normal prostate cells but absent in cancerous prostate cells. Preferably, the protein of this embodiment is selected from the proteins described below which have been designated NDP-1, NDP-2, NDP-3, NDP-4, NDP-5, NDP6, NDP-7, NDP-8, NDP-9, and NDP-10.

According to another aspect, the present invention is directed generally to a method for differentiating a metastatic cell (preferably, prostate) from a non-metastatic cell (preferably prostate) comprising determining the presence or absence of a nuclear matrix protein unique to a metastatic cell or a non-metastatic cell. In particular, nuclear matrix proteins of the prostate are disclosed herein which are capable of differentiating between a metastatic cancer cell and non-metastatic cell of the prostate.

According to another aspect, the present invention is directed to a purified NMP or a fragment thereof, which is present in metastatic but absent in non-metastatic prostate tumors and absent in normal prostate cells. Preferably, the protein of this embodiment is selected from the proteins described below which have been designated as AM-1 and AM-2.

According to another aspect, the present invention is directed to a purified NMP or a fragment thereof, which is absent in metastatic but present in non-metastatic prostate tumors. Preferably, the protein of this embodiment is selected from the proteins described below which have been designated as G-1 and G-2. These two proteins, G-1 and G-2, are also not present in normal prostate cells.

Preferably, the fragments of the NMPs in the above embodiments are immunogenic fragments. It also is preferable that, in the embodiments discussed above, the NMPs are derived from humans.

Unless otherwise specified, the terms "a", "an" or "the" mean one or more.

The phrase "purified nuclear matrix protein" means a protein of the nuclear matrix which has been separated from at least one cellular component. The phrase covers both purified nuclear matrix proteins produced recombinantly and those produced by extraction from a natural source.

Another embodiment of the present invention is a purified polynucleotide sequence encoding the above-identified NMPs or NMP fragments of the preceding embodiments. Another embodiment is a purified polynucleotide sequence which hybridizes to the polynucleotide sequence encoding the above-mentioned NMPs or NMP fragments.

Another embodiment is a host cell transformed with a polynucleotide sequence encoding the above-mentioned NMPs or NMP fragments. Transformation of a host cell with recombinant DNA may be carried out by conventional techniques known in the art. Where the host is prokaryotic, such as E. coli, competent cells which are capable of DNA uptake can be prepared from cells harvested after the exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with DNA sequences encoding the NMPs of the invention, and a second foreign DNA molecule encoding a selectable phenotype, such as the herpes simplex thymidine kinase gene. Another method is to use a eukaryotic viral vector, such as simian virus 40 (5V40) or bovine papilloma virus, to transiently infect or transform eukaryotic cells and express the protein. EUKARYOTIC VIRAL VECTORS Gluzman (ed.), Cold Spring Harbor Laboratory, 1982.

Isolation and purification of the NMPs or NMP fragments expressed by a transformed host may be carried out by conventional means including preparative chromatography and immunological separations involving monoclonal or polyclonal antibodies. Antibodies provided in the present invention are immuno-reactive with NMP polypeptide or fragments thereof.

Another embodiment is a recombinant expression vector containing the above-mentioned polynucleotide sequences. Preferably, the vector is a virus. Preferred viruses are RNA viruses and preferred RNA viruses are retroviruses. Another preferred vector is a liposome, preferably a target-specific liposome which may be targeted with, for example, an antibody or ligand. Another preferred vector is a plasmid.

Another embodiment is an antibody which binds to the above-mentioned NMPs or NMP fragments. The antibody may be polyclonal or monoclonal. Using the NMPs isolated by the inventors, antibodies have been prepared which are capable of differentiating between cancerous prostate tissue and normal prostate tissue in both the Dunning model and in human tissues. One embodiment of the present invention is directed to these antibodies. Furthermore, another embodiment of the present invention is directed to antibodies which can detect individuals with prostate cancer that has the ability to advance and/or metastasize.

Another embodiment is a method for detecting a cell proliferative disorder in a subject or for detecting individuals at risk of developing a cell proliferative disorder, preferably prostate cancer, comprising contacting a cellular component from the subject with an antibody or nucleic acid probe which binds to a cellular component associated with the cell proliferative disorder. More preferably, the method is a method for differentiating between prostate cancer that has the potential to metastasize and prostate cancer that lacks the potential to metastasize. Preferably, the cellular component is taken from the subject's prostate and is preferably a nucleic acid. Preferably, the nucleic acid is DNA encoding the above-mentioned NMPs or NMP fragments. Also preferred as a nucleic acid is RNA. Another preferred cellular component is the above-mentioned NMPs or NMP fragments. The differentiation method may be practiced by detecting a single NMP and/or its corresponding DNA or a combination of one or more of the above NMPs and/or their DNA.

Preferably, the nucleic acid probe specifically hybridizes to the above-mentioned cellular component. When the reagent is a nucleic acid probe, it is preferably detectably labeled. Preferred labels include a radioisotope, a bioluminescent compound, a chemiluminescent compound, a fluorescent compound, a metal chelate, and an enzyme.

Alternatively, if the cellular component is an NMP or NMP fragment, then an antibody is used which specifically binds to the NMP or NMP fragment. As noted above, the antibody may be monoclonal or polyclonal.

Another embodiment is a method of treating a cell proliferative disorder associated with a protein selected from the group consisting of D-1, D-2, D-3, AM-1, AM-2, NDP-1, NDP-2, NDP-3, NDP4, NDP-5, NDP-6, NDP-7, NDP-8, NDP-9, NDP-10, G-1, and G-2, comprising administering to a subject with the disorder a therapeutically effective amount of an antisense polynucleotide sequence that blocks the sequences encoding the above-mentioned NMPs. In this embodiment, the treatment is designed to block the expression of one or more NMPs which give rise to the cell proliferative disorder. More preferably, the method is a method of inhibiting metastasis of a cell proliferative disorder and preferably the disorder is prostate cancer.

In an alternative method of treatment, instead of using an antisense polynucleotide sequence, a polynucleotide sequence is used which encodes one of the above-mentioned NMPs. In this embodiment, the treatment is designed to provide the subject with one or more NMPs that prevent or ameliorate the cell proliferative disorder.

In another method of treatment, an antibody is administered to the subject which is capable of blocking the function of one or more of the above NMPs.

Another embodiment is a method of gene therapy, comprising introducing into the cells of a host subject an expression vector comprising a polynucleotide sequence encoding one or more of the above-mentioned NMPs. Preferably, the expression vector is introduced into the cells of the host subject ex vivo, yielding transformed cells, and the transformed cells then are reintroduced into the subject. A preferred expression vector for this purpose is an RNA virus, preferably a retrovirus.

Another embodiment of the present invention relates to a method for identifying a composition which blocks or enhances the function of a prostate cell NMP. The inventive method comprises: (a) incubating NMP-containing prostate cells with a test composition under conditions that allow the prostate cells and test composition to interact, and (b)

measuring whether the test composition blocks or enhances the function of the prostate cell NMP.

Another embodiment of the present invention is a kit for detecting a cell-proliferative disorder of the prostate comprising a nucleic acid probe that binds to a polynucleotide sequence encoding one of the above-mentioned NMPs. Preferably, the probe is labeled for ease of detection with a label as described above. Alternatively, the kit may comprise an antibody which specifically binds to one of the above-mentioned NMPs. Still another alternative is to use an oligonucleotide primer in the kit that permits amplification of a target polynucleotide sequence encoding one of the above-mentioned NMPs, for example, by polymerase chain reaction (PCR) amplification.

The NMPs of the invention include fragments, and conservatively substituted variants thereof. Minor modifications of the NMP primary amino acid sequence may result in proteins which have substantially equivalent activity as compared to the NMP polypeptide described herein. Such modifications may be deliberate, as by site-directed mutagenesis, or may be spontaneous, and can include deletion of non-essential amino acids. All of the polypeptides produced by these modifications are included herein as long as the biological activity of the native NMP still exists. Further, deletion of one or more amino acids can also result in a modification of the structure of the resultant molecule without significantly altering its biological activity. This can lead to the development of a smaller active molecule which would have broader utility.

The term "conservative substitution" as used herein denotes the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

Peptides of the invention can be synthesized by the well known solid phase peptide synthesis methods described, for example, by Merrifield, *J. Am. Chem. Soc.* 85: 2149 (1962), and by Stewart and Young, SOLID PHASE PEPTIDES SYNTHESIS 27–62 (Freeman Publ., 1969).

The polyclonal and monoclonal antibodies of the invention are immunoreactive with the NMPs or immunogenic fragments of the NMPs. If desired, polyclonal antibodies can be further purified, for example, by binding to and elution from a matrix to which NMP polypeptide is bound or by utilizing common nuclear matrix proteins to selectively remove non-specific antibodies. Antibodies which consist essentially of pooled monoclonal antibodies with different epitopic specificities, as well as distinct monoclonal antibody preparations are provided. The term "antibody" as used in this invention includes intact molecules as well as fragments thereof, such as Fab and F(ab')$_2$ fragments, which are functionally capable of binding an epitopic determinant of an NMP.

A preferred method for the identification and isolation of antibody binding domains which exhibit binding with NMP is the bacteriophage X vector system. This vector system has been used to express a combinatorial library of Fab fragments from the mouse antibody repertoire in *Escherichia coli*, see Huse et al., *Science* 246: 1275–81 (1989), and from the human antibody repertoire. Nullinax et al., *Proc. Nat'l Acad. Sci. USA* 87: 8095–99 (1990).

As used herein, the term "cell-proliferative disorder" denotes malignant as well as non-malignant (or benign) disorders of the prostate. This term further encompasses hyperplastic disorders of the prostate. The cells comprising these proliferative disorders often appear morphologically and genotypically to differ from the surrounding normal tissue. As noted above, cell-proliferative disorders may be associated, for example, with expression or absence of expression of the NMPs of the invention. Expression of an NMP at an inappropriate time during the cell cycle or in an incorrect cell type may result in a cell-proliferative disorder. The NMP-encoding polynucleotide in the form of an antisense polynucleotide is useful in treating hyperplasia and malignancies of the prostate. When the cell-proliferative disorder is associated with NMP expression, an antisense NMP polynucleotide sequence or NMP binding antibody can be introduced into the prostate cells to block the expression and/or function of the NNP. Alternatively, when the cell proliferative disorder is associated with under-expression or expression of a mutant NMP polypeptide, a polynucleotide sequence encoding the missing or under-expressed NMP can be introduced into the cell.

For purposes of the invention, an antibody or nucleic acid probe specific for an NMP may be used to detect the presence of the NMP polypeptide (in the case of an antibody probe) or polynucleotide (in the case of the nucleic acid probe) in biological fluids or tissues suspected of containing the NMP. Oligonucleotide primers based on any coding sequence region in the NMP sequence are useful for amplifying DNA or RNA, for example by PCR. Any specimen containing a detectable amount of antigen can be used. A preferred sample of this invention is tissue taken from the prostate. Alternatively, biological fluids which may contain cells of the prostate may be used.

The term "subject" as used herein refers to mammals, preferably humans.

Another technique which may also result in greater sensitivity consists of coupling the probe to low molecular weight haptens. These haptens can then be specifically detected by means of a second reaction. For example, it is common to use such haptens as biotin, which reacts with avidin, or dinitrophenol, pyridoxal, and fluorescein, which can react with specific antihapten antibodies.

The method for detecting a cell expressing a particular NMP of the invention or a cell-proliferative disorder associated with an NMP, described above, can be utilized for detection of residual prostate cancer or other malignancies or benign hyperplasia conditions in a subject in a state of clinical remission. Additionally, the method for detecting NMP polypeptide in cells is useful for detecting a cell-proliferative disorder by identifying cells expressing specific NMPs in comparison with NMPs expressed in normal cells. Using the method of the invention, NMP expression can be identified in a cell and the appropriate course of treatment can be employed (e.g., NMP-encoding or antisense gene therapy, as well as conventional chemotherapy). Since the expression pattern of the NMPs of the invention vary with the stage of malignancy of a cell, a sample of prostate tissue can be screened with a panel of NMP-specific reagents, e.g., nucleic acid probes or antibodies to NMPs, to detect NMP expression and diagnose the stage of malignancy of the cell.

The monoclonal antibodies of the invention are suitable for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be performed utilizing immunoassays which are run in either the forward, reverse, or simultaneous modes, including immunohistochemical assays on physiological samples. Alternatively, the antibody of the invention can be used to detect NMPs present in electrophoretically dispersed gel protocols such as Western blots and two-dimensional gels.

The monoclonal antibodies of the invention can be bound to many different carriers and used to detect the presence of NMP. Examples of well—known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention.

In performing the assays it may be desirable to include certain "blockers" in the incubation medium (usually added with the labeled soluble antibody). The "blockers" are added to assure that non-specific proteins, proteases, oranti-heterophilic immunoglobulins to anti-NMP immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgGi, IgG2a, 1gM, etc.) can be used as "blockers. " The "blockers" are used at a level high enough to maintain the proper sensitivity yet inhibit any unwanted interference by mutually occurring cross reactive proteins in the specimen (normally 1–100 $\mu g/\mu l$).

In this description, the term "epitope" denotes any determinant capable of specific interaction with the monoclonal antibodies of the invention. Epitopic determinants usually comprise chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of delectably labeled monoclonal antibody is administered in sufficient quantity to enable detection of the site having the NMP antigen for which the monoclonal antibody is specific.

The dosage of detectably labeled monoclonal antibody for in vivo diagnosis will vary depending on such factors as age, sex, and extent of disease of the individual. The dosage of monoclonal antibody can vary from about 0.001 mg/in², to about 500 mg/in², preferably 0.1 mg/in² to about 200 mg/in², most preferably about 0.1 mg/in² to about 10 mg/rn². Such dosages may vary, for example, depending on whether multiple injections are given, tumor burden, and other factors.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylene-triaminepentacetic acid (DTPA) and ethylenediarninetet-raacetic acid (EDTA) and similar molecules. Typical examples of radioisotopes which can be bound to the monoclonal antibodies of the invention are $^{111}$In, $^{97}$Ru, $^{67}$Ga, Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and para-magnetic isotopes for MRI. Elements which are particularly useful in such techniques include $^{57}$Gd, $^{55}$Mn, $^{162}$Dy, $^{52}$Cr, and $^{56}$Fe.

The monoclonal antibodies of the invention can be used to monitor the course of amelioration of an NMP-associated cell-proliferative disorder. Thus, by measuring the increase or decrease in the number of cells expressing a NMP or changes in NMP present in various body fluids, such as ejaculate or urine, it would be possible to determine whether a particular therapeutic regimen aimed at ameliorating the disorder is effective.

The monoclonal antibodies of the invention can also be used, alone or in combination with effector cells, see Douillard et al., *Hybridoma* 5 (Supp. 1): S139 (1986), for immunotherapy in an animal having a cell proliferative disorder which expresses NMP polypeptide with epitopes reactive with the monoclonal antibodies of the invention.

When used for immunotherapy, the monoclonal antibodies of the invention may be unlabeled or attached to a therapeutic agent. These agents can be coupled either directly or indirectly to the monoclonal antibodies of the invention. One example of indirect coupling is by use of a spacer moiety. These spacer moieties, in turn, can be either insoluble or soluble, see Diener et al., *Science* 231: 148 (1986), and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The drugs which can be conjugated to the monoclonal antibodies of the invention include non-proteinaceous as well as proteinaceous drugs. The terms "non-proteinaceous drugs" encompasses compounds which are classically referred to as drugs, for example, mitomycin C, daunorubicin, vinblastine, and others used to treat cancer.

The proteinaceous drugs with which the monoclonal antibodies of the invention can be joined include immunomodulators and other biological response modifiers. The term "biological response modifiers" encompasses substances which are involved in modifying the immune response in such manner as to enhance the destruction of an NMP-associated tumor for which the monoclonal antibodies of the invention are specific. Examples of immune response modifiers include such compounds as lymphokines. Lymphokines include tumor necrosis factor, the interleukins, lymphotoxin, macrophage activating factor, migration inhibition factor, colony stimulating factor, and interferon. Interferons with which the monoclonal antibodies of the invention can be labeled include alpha-interferon, beta-interferon and gamma-interferon and their subtypes.

In using radioisotopically conjugated monoclonal antibodies of the invention for immunotherapy, certain isotopes may be more preferable than others depending on such factors as tumor cell distribution as well as isotope stability and emission. If desired, the tumor cell distribution can be evaluated by the in vivo diagnostic techniques described above. Depending on the cell proliferative disease some emitters may be preferable to others. In general, alpha and beta particle-emitting radioisotopes are preferred in immunotherapy. For example, if an animal has solid tumor foci a high energy beta emitter capable of penetrating several millimeters of tissue, such as 9%, may be preferable. On the other hand, if the cell proliferative disorder consists of simple target cells, as in the case of leukemia, a short range, high energy alpha emitter, such as Bi, may be preferable. Examples of radioisotopes which can be bound to the monoclonal antibodies of the invention for therapeutic purposes are radioisotopes of I, Y, Cu, Bi, At, Pb, Sc, Pd, Zn, and Re.

Lectins are proteins, usually isolated from plant material, which bind to specific sugar moieties. Many lectins are also able to agglutinate cells and stimulate lymphocytes. Ricin is a toxic lectin which has been used immunotherapeutically. The alpha-peptide chain of ricin, which is responsible for toxicity, may be bound to the antibody of the invention to enable site specific delivery of the toxic effect.

Toxins are poisonous substances produced by plants, animals, or microorganisms, that, in sufficient dose, are often lethal. Diphtheria toxin is a substance produced by Corynebacterium diphtheria which can be used therapeutically. This toxin consists of an alpha and beta subunit which under proper conditions can be separated. The toxic A component can be bound to an antibody and used for site specific delivery to a NMP bearing cell.

The monoclonal antibodies of the invention can be used in combination with alpha-interferon. This treatment modality enhances monoclonal antibody targeting of carcinomas by increasing the expression of monoclonal antibody reactive antigen by the carcinoma cells. Greiner et al., *Science* 235: 895 (1987). Alternatively, the monoclonal antibody of the invention can be used, for example, in combination with gamma-interferon to thereby activate and increase the expression of Fc receptors by effector cells which, in turn, results in an enhanced binding of the monoclonal antibody to the effector cell and killing of target tumor cells.

It also is possible to utilize liposomes with the monoclonal antibodies of the invention in their membrane to specifically deliver the liposome to the tumor expressing NMP. These liposomes can be produced such that they contain, in addition to the monoclonal antibody, such immunotherapeutic agents as those described above which would then be released at the tumor site. Wolff et al., *Biochemical et Biophysical Acta* 802: 259 (1984).

The dosage ranges for the administration of monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents, lower dosages, comparable to those used for in vivo diagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

The present invention also provides a method for treating a subject with an NMP-associated cell-proliferative disorder using an NMP nucleotide sequence. An NMP nucleotide sequence which may encode a suppressor polypeptide may be under-expressed as compared to expression in a normal cell, therefore it is possible to design appropriate therapeutic or diagnostic techniques directed to this sequence. Thus, where a cell-proliferative disorder is associated with the expression of an NMP associated with malignancy, nucleic acid sequences that interfere with NMP expression at the translational level can be used. This approach utilizes, for example, antisense nucleic acid and ribozymes to block translation of a specific NMP mRNA, either by masking that mRNA with an antisense nucleic acid or by cleaving it with a ribozyme. In cases when a cell proliferative disorder or abnormal cell phenotype is associated with the under expression of NMP suppressor for example, nucleic acid sequences encoding UMP (sense) could be administered to the subject with the disorder.

Antisense nucleic acids are DNA or RNA molecules that are complementary to at least a portion of a specific mRNA molecule. Weintaub, *Scientific American* 262: 40 (1990). In the cell, the antisense nucleic acids hybridize to the corresponding mRNA, forming a double-stranded molecule. The antisense nucleic acids interfere with the translation of the mRNA since the cell will not translate a mRNA that is double-stranded. Antisense oligomers of about 15 nucleotides are preferred, since they are easily synthesized and are less likely to be expressed than larger molecules when introduced into the target NMP-producing dell.

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it. Cech, *J. Amer. Med. Assn.* 260:3030 (1988). A major advantage of this approach is that, because they are sequence-specific, only in RNAs with particular sequences are inactivated.

There are two basic types of ribozymes namely, tetrahymena-type (Hasselhoff, *Nature* 334:585 (1988)) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that that sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative disorders which are mediated by NMP. Such therapy requires introduction of the appropriate NMP polynucleotide sequence (antisense or encoding strand) into cells of subjects having the proliferative disorder. Delivery of antisense NMP polynucleotides can be achieved using a recombinant expression vector such as a chimeric virus or a liposome. Disorders associated with under-expression of an NMP or expression of a cancer-associated NMP can be treated using gene therapy with the encoding or antisense nucleotide sequences, respectively.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), inurine mammary tumor virus (MuMTV), and Rous Sarcoma Virus (RSV) A number of additional retroviral vectors can incorporate multiple genes. All of these vectors can transfer or incorporate a gene for a selectable marker so that transduced cells can be identified and generated. By inserting an NMP sequence of interest into the viral vector along with another gene which encodes the ligand for a receptor on a specific target cell, for example, the vector is rendered target specific. Retroviral vectors can be made target specific by inserting, for example, a polynucleotide encoding a sugar, a glycolipid, or a protein. Preferred targeting is accomplished by using an antibody to target the retroviral vector.

Since recombinant retroviruses are defective in one or more genes, they require assistance in order to produce infectious vector particles. Helper cell lines which have deletions of the packaging signal include but are not limited to W2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env by conventional calcium phosphate transfection. These cells are then transfected with the vector plasmid containing the genes of interest. The resulting cells release the retroviral vector into the culture medium.

Other targeted delivery systems for NMP antisense polynucleotides include macromolecule complexes, nanocapsules, microspheres, beads, and lipid-based systems including oil-in-water emulsions, micelles, mixed micelles, and liposomes. Liposomes are artificial membrane vesicles which are useful as delivery vehicles in vitro and in vivo. It has been shown that large unilamellar vesicles (ULV), which range in size from 0.2–4.0 pm can encapsulate a substantial percentage of an aqueous buffer containing large macromolecules. RNA, DNA and intact virions can be encapsulated within the aqueous interior and be delivered to cells in a biologically active form. Fraley et al., *Trends Biochem. Sci.* 6: 77 (1981).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidyiserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a hyposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

In general, surface membrane proteins which bind to specific effector molecules are referred to as receptors. In the present invention, antibodies of the invention are preferred receptors. Antibodies can be used to target liposomes to specific cell-surface ligands, in this case the NMPs of choice. Preferably, the target tissue is prostate tissue. A number of procedures can be used to covalently attach either polyclonal or monoclonal antibodies to a liposome bilayer. Antibody-targeted liposomes can include monoclonal or polygonal antibodies or fragments thereof such as Fab, or $F(ab')_2$, as long as they bind efficiently to an the antigenic epitope on the target cells.

Preparations for parenteral administration include sterile aqueous or nonaqueous solutions, suspensions, and emulsions. Examples of non aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such an those based on Ringer's dextrose), and the like. Preservatives and other additives may also be present such as, for example, antimicrobials, anti-oxidants, chelating agents and inert gases and the like.

The invention also relates to a method for preparing a medicament or pharmaceutical composition comprising the polynucleotides or the monoclonal antibodies of the invention, the medicament being used for therapy of NMP-associated cell proliferative disorders.

The invention is further illustrated by, though in no way limited to, the following examples.

Isolation and Sequencing of Rat Nuclear Matrix Proteins

The G, AT2.1 and MLL sublines of the Dunning R3327 rat prostate adenocarcinoma cell line were utilized. The cells were cultured in RPMI 1640 containing 10% fetal bovine serum, 250 nM dexamethasone, penicillin G and streptomycin both at 100 units/ml. The cells were then harvested and fractionated to isolate nuclear matrix proteins, as described below.

The Dunning R3327 AT2.1 rat prostate tumors were transplanted subcutaneously into male Copenhagen rats and harvested when the tumor weights reached 3–4 grams. Normal rat dorsal prostates were obtained from mature intact male Sprague-Dawley rats (300–350 g) obtained from Charles River (Wilmington, Mass.). Tumor and tissue samples were fractionated to isolate nuclear matrix proteins as described below.

Normal and tumor prostate tissue samples were obtained from patients undergoing surgery for prostate cancer at the University of Pittsburgh Medical Center. Samples were only utilized that could clearly be identified by the pathologist as containing approximately pure populations of the stated cell type.

The nuclear matrix proteins were isolated from the prostate tissues, cells and tumors selected above as taught in Fey, et al., *J. Cell Biol.*, 98:1973–1984, 1988 and Getzenberg, et al., *Cancer Res.*, 51:6514–6520, 1991. The tissue pieces were minced into small (1 mm.sup.3) pieces and homogenized with a Teflon pestle on ice with 0. 5% Triton X-100 in a solution containing 2 mM vanadyl ribonucleoside (RNase inhibitor) to release the lipids and soluble proteins. Extracts were then filtered through a 350 micron nylon mesh and extracted with 0.25M ammonium sulfate to release the soluble cytoskeletal elements. Dnase treatment at 25.degree. C. was used to remove the soluble chromatin. The remaining fractions contained intermediate filaments and nuclear matrix proteins. This fraction was then disassembled with 8M urea, and the insoluble components, which consisted principally of carbohydrates and extracellular matrix components, were pelleted. The urea was dialyzed out, and the intermediate filaments were allowed to reassemble and removed by centrifugation. The nuclear matrix proteins were then ethanol precipitated. All solutions contained freshly prepared 1 mM phenylmethylsulfonylfluoride (PMSF) to inhibit serine proteases, 0.3 $\mu$M aprotonin, 1 $\mu$M leupeptin and 1 $\mu$M pepstatin.

Antibodies to proteins of this fraction were prepared and demonstrated to be localized exclusively in the nucleus and isolated nuclear matrix fraction. The protein composition was determined by resuspending the proteins in 0.1N sodium hydroxide and utilizing the Coomassie Plus protein assay reagent kit (Pierce, Rockford, Ill.) with bovine serum albumin (BSA) as a standard.

For two-dimensional gel electrophoresis, the ethanol precipitated NMPs were dissolved in a sample buffer consisting of 9M urea, 65 mM 3->(3-Cholamidopropyl)-dimethyl-ammonio-1-propanesulfonate (CHAPS), 2.2% ampholytes and 140 mM dithiothreitol. The final pellet containing NMPs represented less than 1% of the total cellular proteins.

The nuclear matrix proteins were separated by the high resolution two-dimensional gel electrophoretic procedure. High resolution two-dimensional gel electrophoresis was carried out utilizing the Investigator 2-D gel system (Genomic Solutions, Chelmsford, Mass). Briefly, one-dimensional isoelectric focusing was carried out for 18,000 V-h using 1-mm×18-cm tube gels after 1.5 h of prefocusing. The tube gels were extruded and placed on top of 1-mm sodium dodecyl sulfate Duracryl (Genomic Solutions, Chelmsford, Mass.) high tensile strength polyacrylamide electrophoresis slab gels, and the gels were electrophoresed with 12° C. constant temperature regulation for approximately 5 hours. Gels were fixed with 50% methanol and 10% acetic acid. After thorough rinsing and rehydration, gels were treated with 5% glutaraldehyde and 5 mM dithiothreitol after buffering with 50 mM phosphate (pH 7.2). The gels were stained with silver stain (Accurate Chemical Co., Inc., Westbury, N.Y.) or transferred to PVDF (Immobilon, Millipore Corporation) as follows.

Fifty micrograms of nuclear matrix protein were loaded for each gel. Protein molecular weight standards were Silver Standards from Diversified Biotechnology (Newton Centre, Mass.). Isoelectric points were determined using carbamylated standards from Gallaro-Schlesiwger, Inc. (Carle Place, N.Y.) and Sigma Chemical Co. (St. Louis, Mo.). Multiple gels were run for each sample, and multiple samples run at different times. Only protein spots clearly and reproducibly observed in all the gels of a sample type were counted as actually representing the nuclear matrix components. The gels were analyzed using the BioImage Electrophoresis Analysis System (BioImage, Ann Arbor, Mich.) which matches protein spots between gels and databases the gels and protein spots. A unique combination of Chaps detergent and ampholyte was used to run these gels. Since tissues were used to isolate these nuclear matrix proteins, the resulting proteins are tissue nuclear matrix proteins which differ significantly from nuclear matrix proteins obtained from cell cultures.

A unique staining methodology was used to stain the high resolution two-dimensional gels. Utilizing a ZnCl negative staining technique, novel nuclear matrix proteins were identified without having to sequence them.

The protein spot of interest was excised from many gels, collected and concentrated into a single band in agarose using an SDS/PAGE system. The agarose slice was then subjected to the Edman Degradation process yielding its amino acid sequence.

The following rat proteins were identified:

TABLE 1

| Protein | Protein Sequence | Homologies | Antibodies | Rat Reactivity | Human** Reactivity |
|---|---|---|---|---|---|
| D-1<br>Mol. Wt.<br>Of 63 kD<br>pI 8.55 | Peptide 1<br>ITGLNMVEM<br>(SEQ ID NO: 1) | None | Polyclonal (2D) | Western blot - not useful | ? |
| | Peptide 2<br>YGPQYGHPPPPPPPPDYGPHADSPV<br>(SEQ ID NO: 2) | 96% homology w/poly proline region of hnRNP L* | poor by western | | |
| | Peptide 3<br>IQHPSNVLHFFNAPLEVTEENFFEI<br>(SEQ ID NO: 3) | 100% homology with C-terminal portion of hnRNP L* | | | |
| D-2<br>Mol. Wt.<br>Of 40 kD<br>pI 5.91 | Peptide 1<br>DESTLQGF<br>(SEQ ID NO: 4) | None | polyclonal (2D) | western blot- picks up protein in G, AT-2, AT-6, MLL | Western blot - identifies human Pca but not normal tissue |
| | Peptide 2<br>ALQDKV<br>(SEQ ID NO: 5) | None | good | | |
| D-3<br>Mol. Wt.<br>Of 33 kD<br>pI 6.97 | Peptide 1<br>RL???TKPMVNLIK<br>(SEQ ID NO: 6) | None | polyclonal (2D) good | western blot - pickups up protein in G, AT-2, AT-6, MLL | |
| AM-1<br>Mol. Wt.<br>Of 40 kD<br>pI 6.73 | Peptide 1<br>VSNTPLPGVFTK<br>(SEQ ID NO: 7) | | polyclonal (2D) good | western blot - picks up protein in the metastatic lines AT-2, AT-6, MLL but not G immunofluorescence/ confocalnuclear punctuate | western blot - identifies some human Pca |
| AM-2<br>Mol. Wt.<br>36 kD<br>pI 8.33 | Peptide 1<br>NLDLDSIIAEVK<br>(SEQ ID NO: 8) | | polyclonal (2D) poor | | |

TABLE 2

| Protein | Mol wt (kD) | PI |
|---|---|---|
| NDP-1 | 95 | 6.74 |
| NDP-2 | 57 | 8.33 |
| NDP-3 | 57 | 8.0 |
| NDP-4 | 47 | 5.26 |
| NDP-5 | 47 | 5.80 |
| NDP-6 | 41 | 6.83 |
| NDP-7 | 37.2 | 7.05 |
| NDP-8 | 36.9 | 7.35 |
| NDP-9 | 35 | 6.25 |
| NDP-10 | 32.5 | 5.46 |
| G-1 | 55 | 6.48 |
| G-2 | 52 | 6.93 |

In the above Tables 1 and 2, molecular weight and pI were determined by comparison to standards of known molecular weight and pI.

Production of Antibodies

Polyclonal antibodies were made in New Zealand white rabbits using the D-2 peptide 2 sequence (see above table) conjugated to KLH. In addition, an antibody was produced against a gel spot isolated from the higher resolution two-dimensional gels corresponding to AM-1. The peptide or spot was administered at a concentration of 150 micrograms/ mil which included 0.5 ml of Freund's adjuvant (FCA) intradermally into the back of a rabbit. Five boosts were administered at 3-week intervals. The concentration of peptide or spot at each boost was 100 micrograms/ml, including 0.5 ml FCA.

Testing the Antibody

Nuclear matrix proteins from both normal and tumor tissue were separated on SDS/PAGE. Western analysis was performed using antisera as the primary antibody (1:100) and HRP labeled goat anti-rabbit (1:20,000) as the second antibody. Sera from the rabbit prior to injection with the antigen was used as an internal control.

Antibody Results

Using the Western analysis, the D-2 antibody is able to detect protein in human prostate tumor samples while it is unreactive to proteins in matched normal samples. The antibody is also able to detect the D-2 protein in all the Dunning tumor cell lines from where it has been identified.

When the Dunning tumors or cell lines are stained with the AM-1 antibody, reactivity is only found in the metastatic lines and is not found in any of the non-metastatic lines that were tested.

Obtaining The Counterpart Human NMPs

Using the rat D-2 and AM-1 antibodies described above, counterpart human NMPs were partially purified and characterized from human prostate tissue samples. Human prostate tissue samples were subjected to a similar technique to the one described above by which the rat NMPs were isolated. The resulting gels contained various bands representing separated human NMPs. The rat D-2 and AM-1 antibodies were applied to the bands to see if they would bind to a particular band. In both cases, the two antibodies bound to two distinct bands representing the counterpart human NMPs. Comparison of these bands to known standards indicated that the human D-2 NMP had a molecular weight and a pI about the same as the rat D-2 NMP (approximately 40 kD and a pI of approximately 5.91). Similarly, the human AM-1 NMP had a molecular weight and a pI about the same as the rat D-2 NMP (approximately 40 kD and a pI of approximately 6.73).

In addition, the rat AM-1 antibody was used to stain human prostatic tissues to determine if the antibody will be able to separate metastatic and non-metastatic tumors in humans as it is able to do in the rat model. Immunoblot and immunohistochemical studies with this antibody raised against the rat AM-1 NMP react with human prostate tumor tissue and provide the evidence that this metastatic disease specific NMP also exists in human prostate cancer tissues. The anti-AM-1 antibody stains some human prostate cancers, but not normal prostate tissue. NMPs have been screened from tissues from 13 patients undergoing radical prostatectomy for prostate cancer. Immunoblot analysis reveals that three out of the 13 patients (23%) had positive staining only in the tumor and five (38%) had a significant amount of staining in the tumor with a minor amount noted in the normal tissues. It is hypothesized that positive staining in these patients may correlate with disease that has the ability to metastasize.

While the invention has been described in detail and with reference to specific embodiments thereof, it will be apparent to one skilled in the art that various changes and modifications can be made therein without departing from the spirit and scope of the invention.

What is claimed is:

1. An isolated or purified protein which is present in cancerous human prostate cells but absent in normal human prostate cells, wherein said protein is obtained from cancerous human prostate cells, said protein has a molecular weight of about 40 kD, said protein has a pI of about 5.91, and a partial amino acid sequence of said protein amino acid SEQ ID NO:5.

2. An isolated or purified peptide consisting of the amino acid sequence of SEQ ID NO:5.

* * * * *